United States Patent
Cassily et al.

[11] Patent Number: 5,743,744
[45] Date of Patent: *Apr. 28, 1998

[54] METHOD AND APPARATUS FOR MEASURING AND ENHANCING NEURO-MOTOR COORDINATION

[75] Inventors: James F. Cassily, Wyoming; James B. Lagerkvist, Royal Oak, both of Mich.

[73] Assignee: Synaptec, LLC, Wyoming, Mich.

[*] Notice: The term of this patent shall not extend beyond the expiration date of Pat. No. 5,529,498.

[21] Appl. No.: 656,061

[22] Filed: May 31, 1996

Related U.S. Application Data

[63] Continuation of Ser. No. 139,568, Oct. 20, 1993, Pat. No. 5,529,498.

[51] Int. Cl.⁶ .................................................. G09B 19/00
[52] U.S. Cl. .......................... 434/258; 434/116; 434/238; 340/825.19
[58] Field of Search .................................... 434/114, 116, 434/185, 236–238, 258, 307 R, 308, 350, 362, 365; 340/384.1, 384.3, 500, 573, 825.06, 825.19, 825.57, 825.7, 825.71, 825.77; 395/927; 119/712, 718; 128/732, 733, 736; 84/470 R, 477 R, 484, 714

[56] References Cited

U.S. PATENT DOCUMENTS

| | | |
|---|---|---|
| 3,498,169 | 3/1970 | Gollen . |
| 3,771,407 | 11/1973 | Leonard . |
| 3,905,269 | 9/1975 | Doerksen et al. . |
| 3,919,915 | 11/1975 | Isbell . |
| 3,942,516 | 3/1976 | Glynn et al. . |
| 4,024,789 | 5/1977 | Humphrey et al. . |
| 4,078,469 | 3/1978 | Calvin . |
| 4,089,246 | 5/1978 | Kooker . |
| 4,120,229 | 10/1978 | Ota . |
| 4,322,744 | 3/1982 | Stanton . |
| 4,325,697 | 4/1982 | Regan et al. . |
| 4,364,299 | 12/1982 | Nakada et al. . |
| 4,392,830 | 7/1983 | Salzman et al. . |
| 4,402,244 | 9/1983 | Nakada et al. . |
| 4,406,208 | 9/1983 | Nazer . |
| 4,432,266 | 2/1984 | Nakada . |
| 4,437,381 | 3/1984 | Chen . |
| 4,484,507 | 11/1984 | Nakada et al. . |
| 4,630,518 | 12/1986 | Usami . |
| 4,651,145 | 3/1987 | Sutter . |
| 4,651,612 | 3/1987 | Matsumoto . |
| 4,736,751 | 4/1988 | Gevins et al. . |
| 4,883,067 | 11/1989 | Knispel et al. . |
| 4,919,030 | 4/1990 | Perron, III . |
| 4,919,143 | 4/1990 | Ayers . |
| 4,928,704 | 5/1990 | Hardt . |
| 4,983,125 | 1/1991 | Smith et al. . |
| 5,215,468 | 6/1993 | Lauffer et al. . |
| 5,302,132 | 4/1994 | Corder . |
| 5,421,236 | 6/1995 | Sanger . |
| 5,511,982 | 4/1996 | Pigache et al. ..................... 434/258 X |

FOREIGN PATENT DOCUMENTS

WO9214229  8/1992  WIPO .

OTHER PUBLICATIONS

*Keyboard Magazine Review*, "Jeanius Electronics Russian Dragon," Nov., 1990.

Product brochure entitled "Russian Dragon Timing Accuracy Meter," published by Jeanius Electronics, San Antonio, TX, Apr. 24, 1990.

*Primary Examiner*—Joe Cheng
*Attorney, Agent, or Firm*—Van Dyke, Gardner, Linn & Burkhart, LLP

[57] ABSTRACT

A method and apparatus for measuring and enhancing the neuro-motor coordination of humans and animals includes generation of a non-visual periodic reference signal that is supplied to the user. A response is received from the user of that user's perception of an occurrence of the periodic reference signal. A non-visual feedback signal is derived as a function of the occurrence of the reference signal and the user response. The non-visual feedback signal is supplied to indicate to that user the temporal relationship of the user's response and the occurrence of the periodic reference signal. The non-visual signal may be in the form of an audio feedback signal or may be a tactile feedback signal.

20 Claims, 6 Drawing Sheets

METHOD AND APPARATUS FOR MEASURING AND ENHANCING NEURO-MOTOR COORDINATION

This is a continuation of application Ser. No. 08/139,568, filed Oct. 20, 1993, now U.S. Pat. No. 5,529,498.

BACKGROUND OF THE INVENTION

This invention relates generally to physiological responses in human an non-human animals, and more particularly to measuring and enhancing the neuro-motor coordination of human and non-human subjects, which shall be referred to as "users." The invention may find application in therapy for injury to neuro-motor functions, in producing an enhanced sense of rhythm in users, in testing the reflexes of individuals and even in educational games. Advantageously, the invention can be practiced notwithstanding a complete loss of any one sensory function of the user.

Biofeedback therapy has long been utilized in order to enhance a sense of well-being in individuals. Biofeedback therapy includes monitoring the brain waves of the subject and indicating to the subject when alpha waves are being produced. The user is then able to produce alpha waves more often by knowing when they occur. Alpha waves are believed to be physiologically, as well as psychologically, beneficial to the individual. Although much research remains to be performed, it is believed that the production of various enzymes affecting the neuro-transmitting capabilities of the nervous system during alpha waves formation enhances the ability of the body to re-establish injured motor functions.

SUMMARY OF THE INVENTION

The present invention is based upon the discovery that non-visual senses, and in particular the sense of hearing, may have a profound effect on the neuro-motor physiology of the individual. This is because non-visual senses are closely related to neuro-motor coordination. The invention is further based upon a realization that there is a close and important relationship between timing and the sense of hearing. For example, the hearing system is capable of detecting and assimilating minute differences in the arrival of sound waves in order to resolve the direction of the sound source. In contrast, the visual system occupies a different portion of the nervous system from the portion controlling reflex coordination and is more of an impediment than a benefactor to neuro-motor coordination. This distinction can best be demonstrated by the ability of individuals to accurately follow a beat, or retain non-visual stimulus, by closing their eyes, whereas the presence of visual input impairs the individual's performance.

A method of enhancing the neuro-motor coordination of at least one user, according to an aspect of the invention, includes generating a non-visual periodic reference signal and supplying that reference signal to the user. A response is received from the user of that user's perception of an occurrence of the periodic reference signal. A non-visual feedback signal is derived, as a function of the occurrence of the reference signal and the user response, and is supplied to indicate to that user the temporal relationship of the user's response and the occurrence of the periodic reference signal. In a preferred form, the feedback signal is an audio signal that differs in frequency from the reference signal in proportion to the lead or lag temporal deviation of the user's response with respect to the reference signal. Thus, if the reference signal is a percussive chime of 300 cycles per second (CPS) and the user produces a response before a subsequent occurrence of the reference signal, a feedback signal will be produced that is higher than 300 CPS in proportion to the amount of temporal deviation. If the response lags a subsequent occurrence of the reference signal, a non-visual feedback signal will be produced that is lower than 300 CPS in proportion to the amount of temporal deviation.

The receipt by the user of the audio reference signal and the audio feedback signal, in the preferred embodiment, will result in a pair of signals of somewhat different frequencies combined to perform a beat frequency. The beat signal will increase in frequency in proportion to the deviation of the response from the dead center position of the reference signal. As the user response gets closer to the reference signal, the beat signal will decrease in frequency. The result is a tendency of the technique to "draw" the user toward time alignment with the reference. It has been discovered that the process of drawing the user toward time alignment, by the production of ever-decreasing beat frequencies, results in the generation of alpha brain waves in the user, which contributes to enhanced neuro-motor functioning of that individual. Thus, the invention is capable of: a) improving the sense of timing of the individual; b) improving the reflex coordination of the individual; and c) potentially improving the neurological and muscular systems of individuals that are severely traumatized or handicapped.

According to another aspect of the invention, two input events are received, at least one of the input events being performed by a user. A non-visual feedback signal is produced to that user to indicate the temporal relationship of the two input events. Thus, by way of example, this aspect of the invention may be useful to develop tempo coordination between two band members by allowing the members to clap in attempted synchronism, producing the two input events. When the input events occur within a specified temporal deviation of each other, a non-visual feedback signal is generated. When the events are out of specification, no feedback signal is generated. It has been discovered that two individuals will learn to clap in synchronism by closing their eyes and utilizing this technique, with a resulting enhancement of their ability to perform musically together.

Although the invention, as disclosed herein, may be in the form of an audio feedback system, other non-visual signals are possible. For example, deaf individuals may benefit from the invention by the use of a tactile sensor that senses a response, such as a tapping, of the individual and a tactile transducer that produces a reference tactile signal and a tactile feedback tactile signal proportionate in amplitude to the temporal lag or lead of the response to the reference tactile signal.

The invention additionally comprehends the provision of a "N-times" correct response indicator in order to advise the user, or a therapist, of the number of times that an individual is within a specified time alignment with a referenced signal. The tolerance of an acceptable response may be adjustable in order to provide the ability to adjust the degree of difficulty of the system. The invention further comprehends the development of an electronic record of a user's operation of a system according to the invention in order to track that user's neuro-motor development for use in therapy.

These and other objects, advantages and features of this invention will become apparent upon review of the following specification in conjunction with the drawings.

DESCRIPTION OF THE PREFERRED EMBODIMENT

Figure 1:
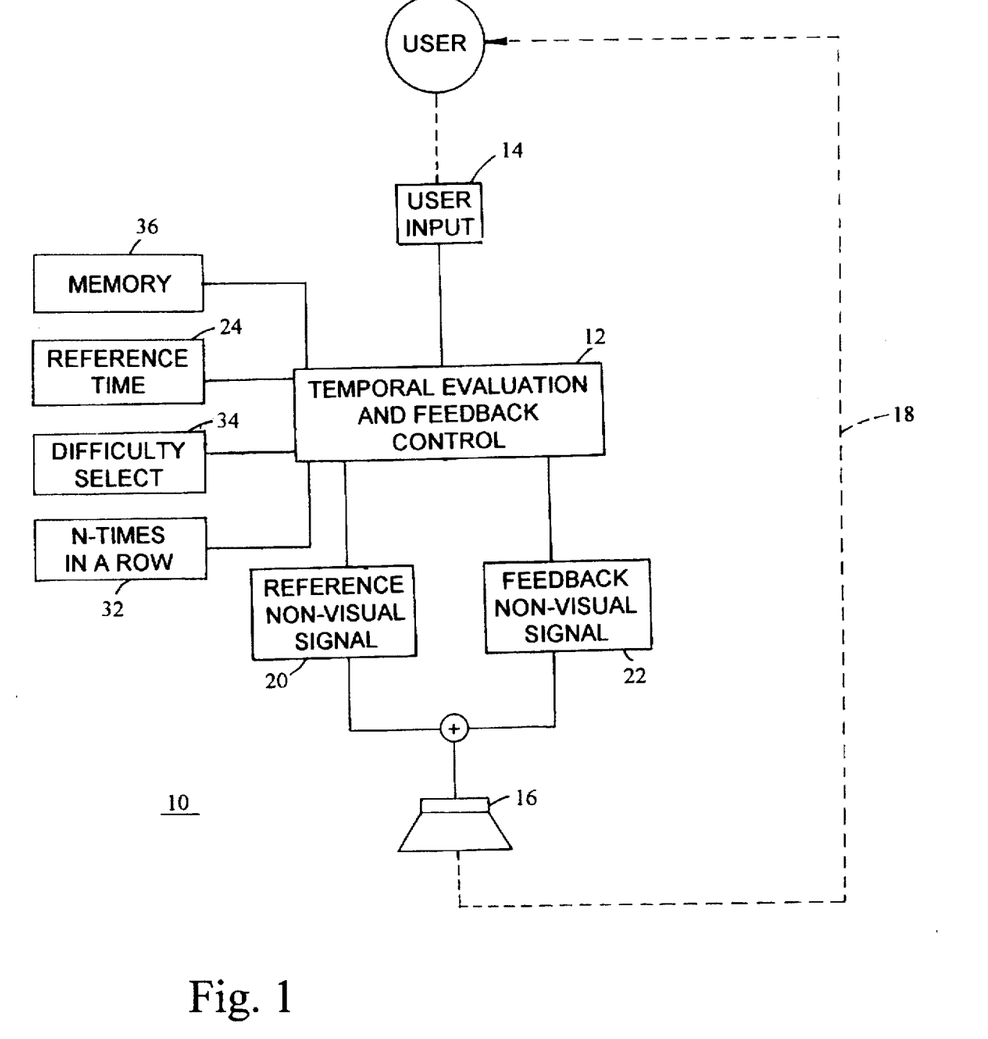
FIG. 1 is a block diagram of a method and apparatus for establishing and enhancing the neuro-motor coordination of a user.

Referring now specifically to the drawings, and the illustrative embodiments depicted therein, a neuro-motor coordination measuring and enhancing system 10 includes a temporal evaluation and feedback control 12 which receives a response input from a user at 14 and produces a non-visual reference and feedback signal with an output generator 16 (FIG. 1). The non-visual output produced by generator 16 is fed back to the user as indicated by the phantom line 18. Output generator 16 is supplied with a signal that is a composite of an output from a reference signal generator 20 and a feedback signal generator 22. Neuro-motor coordination measuring and enhancing system 10 additionally includes a reference time generator 24, which may be an internal clock source supplied to control 12.

Figure 2A:
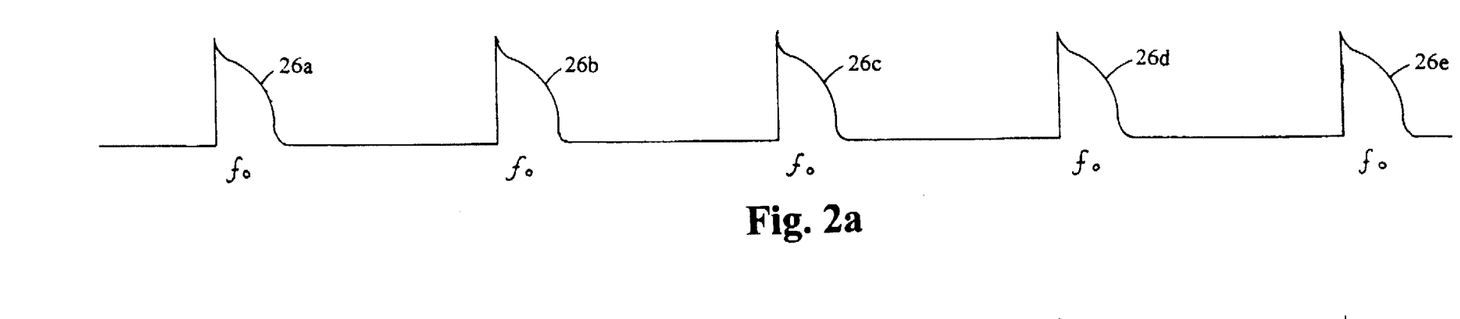
FIGS. 2a, 2b and 2c are timing diagrams of user responses and audio feedback signals generated according to the invention.
Figure 2B:
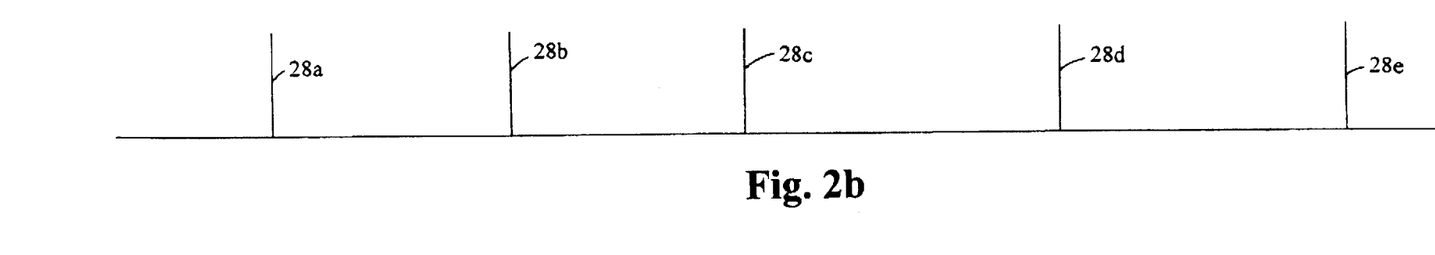
Figure 2C:
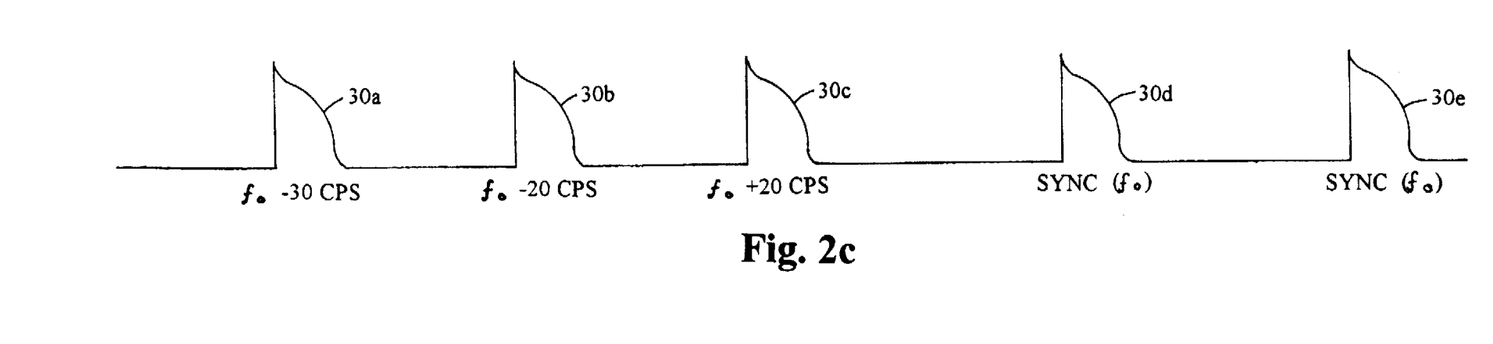

Control 12 causes reference signal generator 20 to produce a periodic reference signal 26a–26e in unison with reference time generator 24, as illustrated in FIG. 2A. The reference signal may be a pure tone or may be a percussive tone, such as a bell chime or other percussive burst. The reference signal is presented to the user through output generator 16 and feedback channel 18. The user supplies a response 28a–28e via user input device 14 that corresponds with the user's expectation of a subsequent occurrence of reference signal 26a–26e, as indicated in FIG. 2b. The user's response may be detected by touch, impact, motion, pressure, proximity, sound, moisture or any other parameter that may be manipulated by a user. For example, an impact sensor mounted to the foot of the user could detect a foot-tapping or a dancing motion. A touch sensor on a housing could detect a user hand-tapping. A microphone could detect a user clapping hands. Temporal evaluation and feedback control 12 determines whether response 28a–28e occurs prior to, or after, a subsequent reference signal 26a–26e and the extent of the temporal lead or lag thereof, and produces a non-visual feedback signal 30a–30e, illustrated in FIG. 2C, through feedback signal generator 22. Feedback signal 30a–30e is produced concurrently with the user's response 28a–28e and has a frequency that differs from that of reference signal 26a–26e in proportion to the amount of temporal lead or lag of the response from the reference signal. Thus, because the response 28a lags the reference signal 26a, the feedback signal 30a will have a reduced frequency ($f_o$-30 CPS) to produce a lower tone, as indicated at 30a. In contrast, the user response 28c leads the reference signal 26c. Therefore, the resultant feedback signal 30c will have a frequency ($f_o$+20 CPS) that is proportionately higher than the reference signal relative to the degree of lead in order to produce a tone that is higher in pitch. When the user response 28d, 28e occurs dead center with a reference signal 26d, 26e, the feedback signal 30d, 30e has the same pitch as the reference signal but is richer in tone resulting from an increase in amplitude. The feedback signal, which is produced concurrently with the user response, may either extinguish after a predetermined period or may decay until the next response is received, at which time the feedback signal is repeated with the appropriate pitch.

Figure 3:
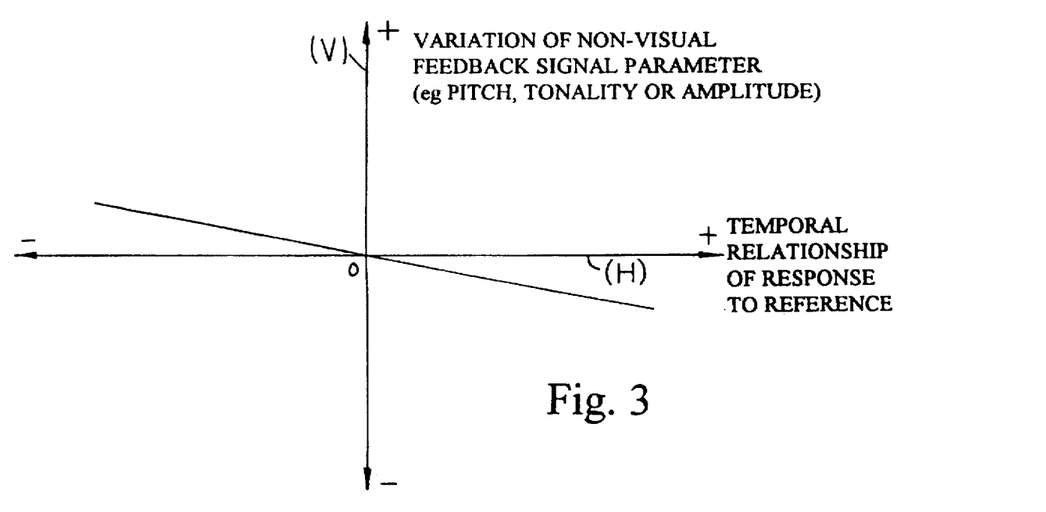
FIG. 3 is a diagram illustrating the relationship between the feedback signal parameter and the temporal relationship of the response to the reference signal.

The feedback signal 30 may vary from the reference signal 26 in either pitch, tonality (i.e., tambour or brilliance) or amplitude. The degree of variation of the selected parameter from that of the reference signal is a function of whether the user response leads or lags the reference signal in time and the amount of the lead or lag. This relationship is illustrated in FIG. 3 in which a response which occurs dead center with the reference signal is indicated at the origin O. If the response 28 arrives before the reference signal 26, as indicated to the left of the vertical axis (V), the pitch, tonality or amplitude parameter of the feedback signal 30 is greater than that of the reference signal, as indicated by the line extending above the horizontal axis (H). If the response 28 arrives after the reference signal 26, the pitch, tonality or amplitude of the feedback signal will be less than that of the reference signal, as indicated by the sloping line below the horizontal axis (H) to the right of the vertical axis (V). Of course, the pitch, tonality, or amplitude of the feedback signal could, alternatively, be less than that of the reference signal for temporally leading responses and more than that of the reference signal for temporally lagging responses. As also indicated in FIG. 3, the degree of variation of the feedback signal from the reference signal is a function of the amount that the response differs from dead center.

In the case where the pitch parameter is utilized to provide non-visual feedback to the user, the feedback signal will vary from the reference signal in proportion to the amount of deviation between the response and the reference signal. Because the feedback signal and the reference signal will either overlap or be produced closely in time, the difference between the two will produce a beat frequency equal to the difference in frequency between these two signals, which will be perceived as a low pitch tone by the user. This beat signal will decrease in frequency the closer the user response is to dead center time alignment with respect to the reference signal. Thus, the system tends to "draw" the user toward improved time alignment.

Neuro-motor coordination measurement and enhancement system 10 additionally includes a "N-time" indicator 32 in order to indicate when the user has produced responses 28, which deviate from reference signal pulses 26 within a specified temporal tolerance a given number of times (N) in a row. Indicator 32 may be a visual indicator, such as an indicator light, or it may be an audio indicator, such as an increase in amplitude of the feedback signal 30. A difficulty select module 34 may be provided to adjust the specification of the response temporal tolerance that must be satisfied in order to activate the N-times indicator 32. This allows the user or therapist to adjust the system to the capabilities of the user. Alternatively, control 12 could be programmed to automatically adjust difficult select module 34 in response to appropriate illumination of the N-time indicator 32. Control 12 could additionally include a memory 36 in order to retain a user's performance record utilizing system 10 over a period of time. This will be especially useful for a therapist in order to evaluate the progress of a patient undergoing therapy using system 10.

Reference time generator 24 may include, for selection, a number of internally generated sounds that are stored in semi-conductor memory. These could include bell sounds, other percussive sounds, pure tones, or the like. Alternatively, reference time generator 24 could respond to an external sound source in order to import a music track. This will allow the temporal evaluation and feedback control 12 to analyze the track in order to develop a reference signal that occurs concurrent with particular characteristics of the music track, such as percussive bursts. In this manner, the reference signal could be derived from an extensive array of potential sources but in all cases control. 12 determines whether the user response temporally leads or lags the reference signal, and by what degree.

Figure 4:
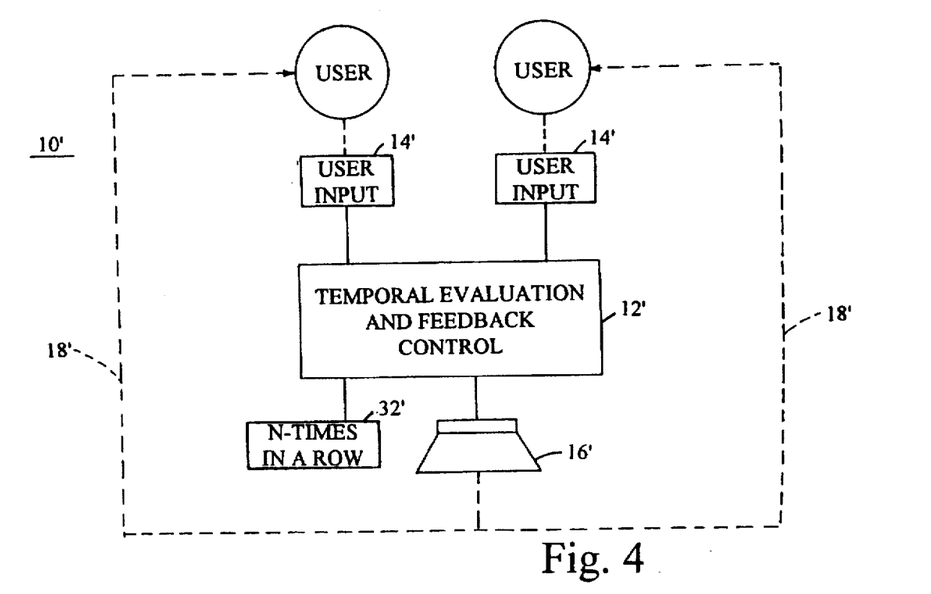
FIG. 4 is a block diagram of a method and apparatus according to an alternative embodiment of the invention.

In an alternative embodiment, a neuro-motor coordination measuring and enhancing system designated 10' receives a pair of user inputs 14' (FIG. 4). A temporal evaluation and feedback control 12' compares responses received from both user inputs 14' to determine whether the responses, or events, occur within a specified temporal tolerance. If so, control 12' produces a feedback signal that is supplied by output generator 16' to both users over feedback paths 18'. The feedback signal generated by control 12' may be an audio chime, a click or any suitable non-visual signal. The two user inputs 14' may be any of the type set forth for user input 14. System 10' differs from system 10 in that temporal evaluation and feedback control 12' does not treat either user generated input event as a reference. Rather, the two user inputs are evaluated to determine how closely they occur together but not which one occurs first. The feedback signal produced on feedback signal generator 22' will, thus, be presented or not presented, as a result of whether or not the two events occur within a specified temporal tolerance of each other. In the illustrated embodiment, the feedback signal will have a characteristic sound that does not vary with the time difference between events. A N-times indicator 32' will indicate when the number of times that two users produce responses within a specified temporal tolerance of each other exceed a given number in a row. System 10' is useful to encourage two individuals to establish a synchronized rhythm together. Thus, the two users touching their individual touch sensors, or clapping into individual microphones, will evoke a feedback signal from signal generator 22' only when they coordinate their rhythms. When a predetermined number of satisfactory responses are obtained in a row, indicator 32 will indicate to the users that, at least momentarily, mutual time alignment has been achieved.

Figure 5:
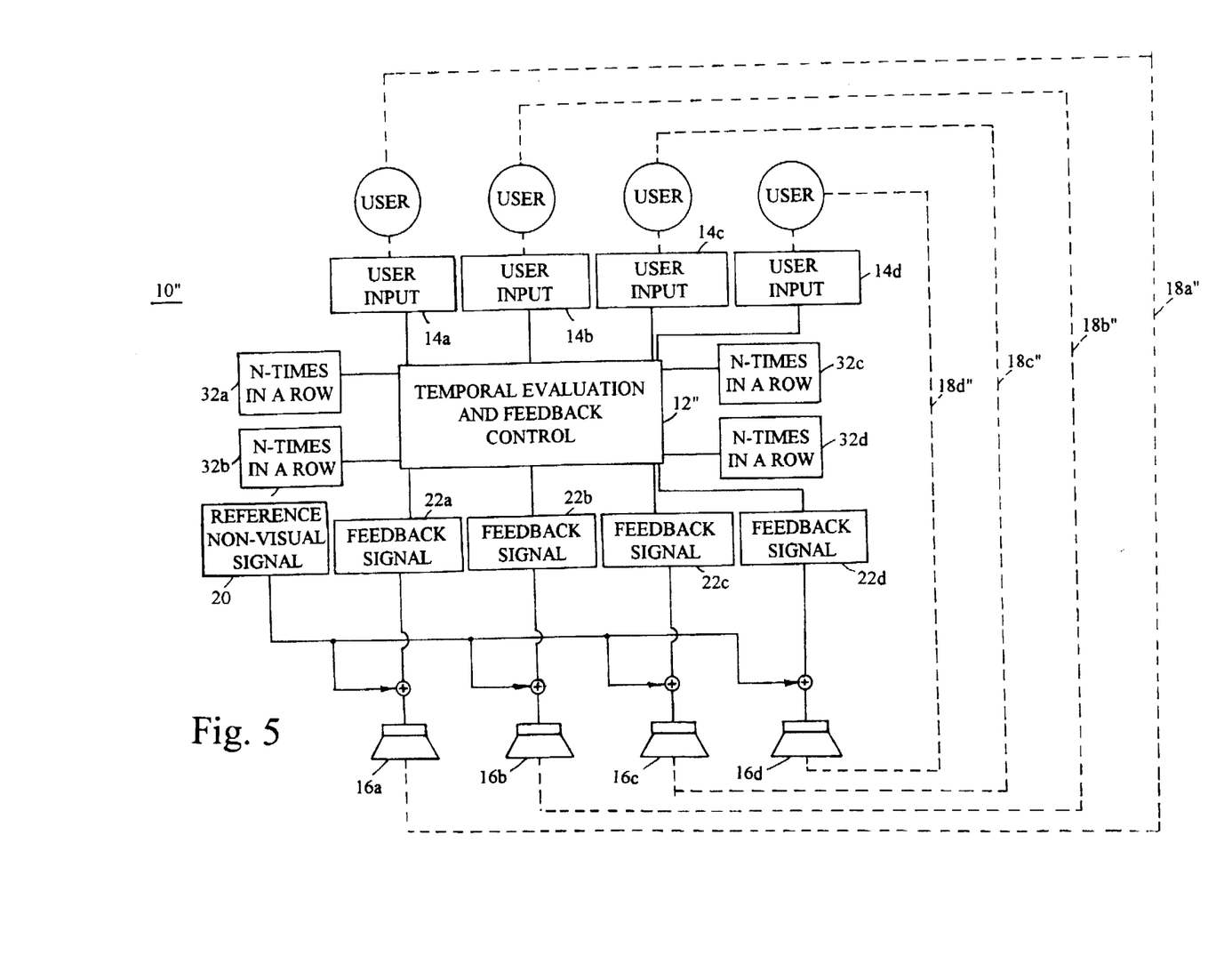
FIG. 5 is a block diagram of a method and apparatus according to a second alternative embodiment of the invention.

FIG. 5 illustrates an alternative embodiment of a neuro-motor coordination measuring and enhancing system 10" in which a plurality of output generators 16a, 16b, 16c and 16d are each supplied with an output from reference signal generator 20 and from one of feedback signal generators 22a, 22b, 22c and 22d. A temporal evaluation and feedback control 12" receives inputs from user response inputs 14a, 14b, 14c and 14d. System 10" is for use with multiple users, each of whom receives a reference signal from reference signal generator 20 and a feedback signal from a feedback signal generator 22a–22d. The signals are coupled by output generators 16a–16d over separate feedback paths 18a"–18d" provided individually for each user. Each user responds with the user inputs 14a–14d provided to that user. Control 12" causes each feedback signal generator 22a–22d to produce a feedback signal that is a function of the temporal deviation of that user's response from the reference signal, concurrently with each user's response. In this manner, each user is provided with a feedback signal that is a function of the time alignment of that user with respect to the reference signal. Thus, system 10" could be utilized as an educational or therapeutic game to determine which of the users may be the first to achieve N-times in a row as indicated by respective indicators 32a, 32b, 32c and 32d.

Figure 6:
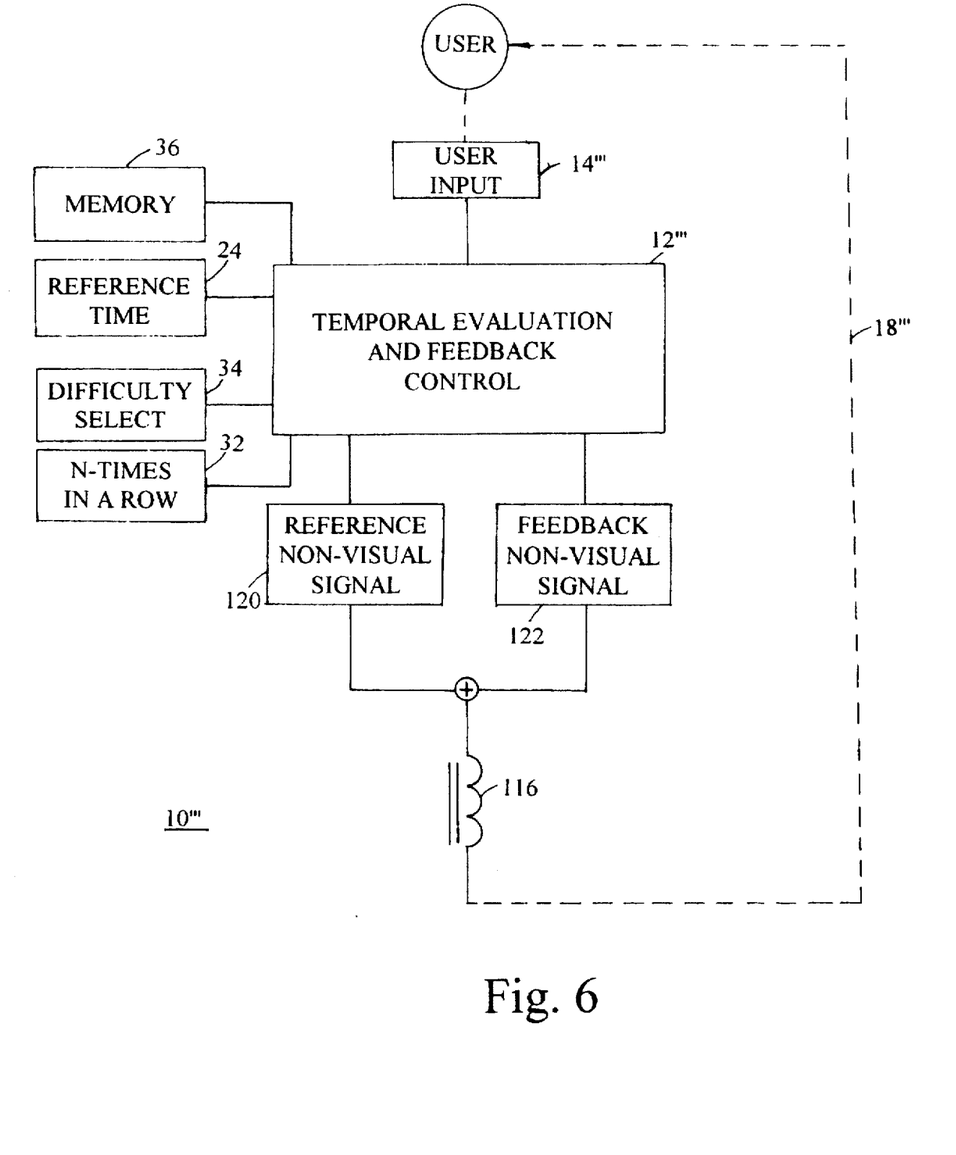
FIG. 6 is a block diagram of a method and apparatus according to a third alternative embodiment of the invention.

In FIG. 6, a neuro-motor coordination measurement and enhancement system 10''' includes a tactile output generator 116 that generates a tactile signal that is a combination of a tactile reference signal, produced by reference signal generator 120 and a tactile feedback signal, produced by a feedback signal generator 122. Because tactile signals may be sensed by individuals who are deaf, system 10''' allows the invention to be practices notwithstanding the inability of the user to hear sounds. Output generator 116, which is schematically illustrated as a motion-producing solenoid, will produce a reference signal that will be sensed by the user's touch and a feedback signal that will be concurrently produced when the user responds through input 14''' to the user's perception of when the reference signal will next occur. The control 12''' will cause feedback signal generator 122 to produce a tactile feedback signal that varies from the reference signal by a detectable manner, such as a decreased amplitude for leading responses and an increased amplitude for lagging responses.

Figure 7:
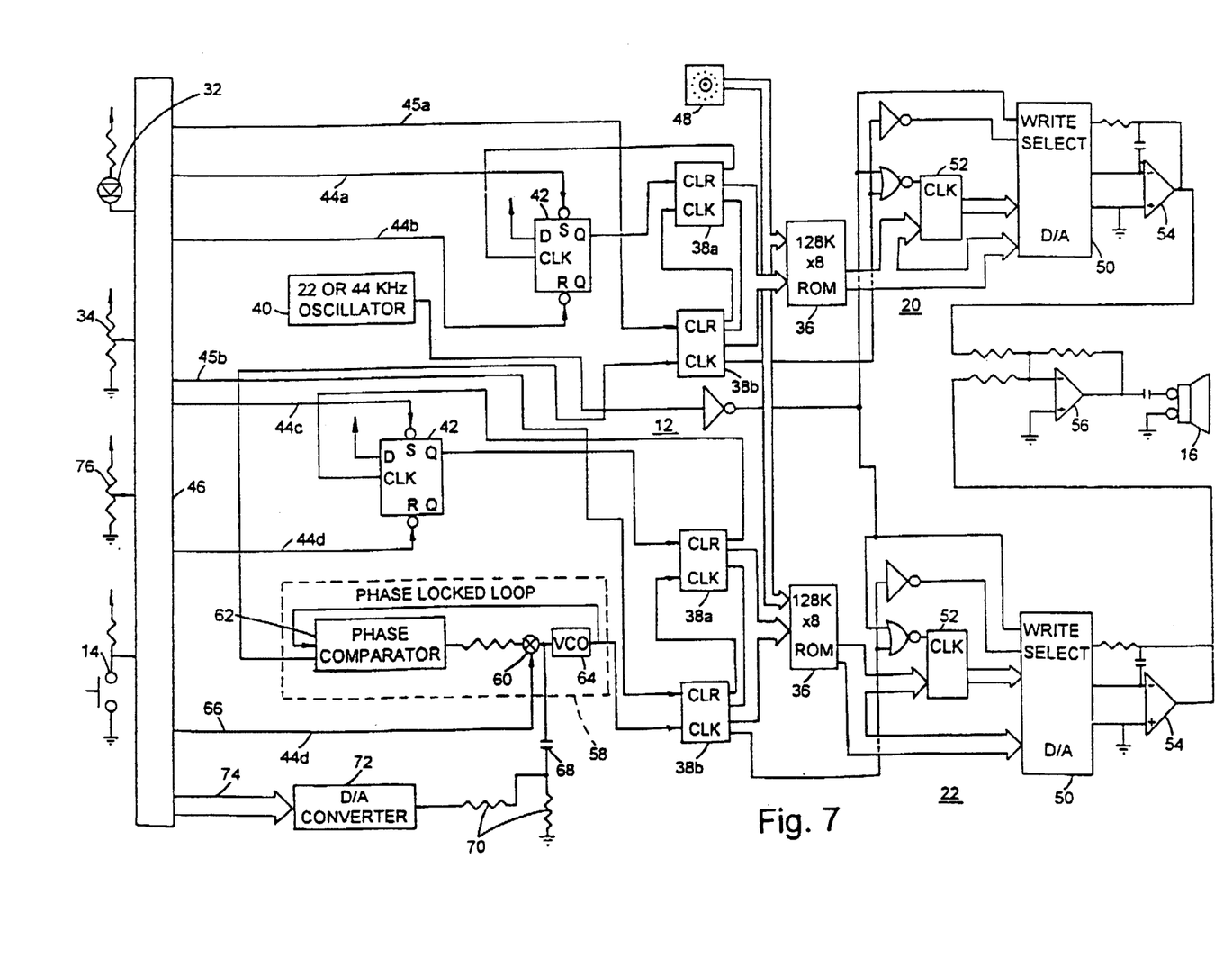
FIG. 7 is a schematic block diagram of an electronic control useful in practicing the invention.

Referring now to FIG. 7, both reference signal generator 20 and feedback signal generator 22 include a read-only memory (ROM) address generator 36 for which two 12-bit counters 38a and 38b are cascaded to give 13 or more address bits to the ROM 36. The counters are clocked from either a master clock 40 or from a signal that is derived from the master clock 40 but has been frequency shifted, as will be set forth in more detail below. A D-type flip-flop 42 is used to detect address overflow and reset the address counters 38a and 38b. The set and reset inputs of flip-flops 42 are driven by outputs 44a, 44b, 44c and 44d of a microprocessor 46. Outputs 44a–44d perform the sound cancel and sound start functions for both the reference signal and the feedback signal, respectively. Microprocessor inputs 45a and 45b confirm the status of the reference signal and feedback signal, respectively. The upper addresses to the ROMs 36 are generated by a user accessible binary coded rotary switch 48 in order to allow the user to select one of several stored sounds to be emitted.

A 12-bit digital-to-analog converter (D/A) 50 converts the binary output of ROM 36 to an analog signal in conjunction with a four-bit latch 52. The most significant byte of a value pair is stored in the lower of the two addresses. As data is read from the ROM, it is either stored in the latch, as the least significant four bits of an address, or it is written directly to the D/A converter 50 along with the latch data in order to make up a 12-bit value. In the illustrated embodiment, a one megabyte ROM, organized 128 K by eight bits, provides a playback time of 744 milliseconds per sound segment. The outputs of D/A converters 50 are buffered at 54 and combined in an op-amp mixer 56. Mixer 56 is designed to be self-limiting in order to avoid overloading output generator 16, which, in the illustrated embodiment, is an audio speaker.

In order to play back ROM data at a slightly different pitch, feedback signal generator 22 is clocked by the output from a phase-lock-loop 58. Within phase-lock-loop 58, an analog switch 60 is placed between the output of a phase comparator 62 and the input of a voltage-controlled-oscillator (VCO) 64. Analog switch 60 is controlled by an output 66 of microprocessor 46. The input to VCO 64 is also connected to a capacitor 68, which forms part of a low-pass filter between phase comparator 62 and the VCO input.

However, the normally grounded end of capacitor 68 is connected through a resistor network 70 to the output of a digital-to-analog (D/A) converter 72, which is controlled by an output 74 of microprocessor 46.

In operation, microprocessor 46 sets the output of D/A converter 72, via output 74, to one-half (0.5) scale and closes analog switch 60. This allows phase-lock-loop 58 to lock onto the frequency of master clock 40. When a user response is detected by the closing of response input 14, microprocessor 46 calculates the required clock frequency deviation. The microprocessor then opens the analog switch 60 and stores a new value to D/A converter 72 that is greater than or less than the one-half (0.5) scale as required to shift the VCO frequency. The capacitor acts to hold this input to the VCO long enough to play back the sound at the different clock rates which, in the illustrated embodiment, is approximately one second. When the control 12 has completed its playback cycle, microprocessor 46 cancels the reference and feedback signals and resets the D/A value back to one-half (0.5) scale and then closes the analog switch.

Difficulty select potentiometer 34 is provided as an input to microprocessor 46 in order to vary the amount of pitch change versus deviation from correct timing to allow the microprocessor to determine a multiplier in the calculation for the pitch offset. This input additionally establishes the amount of deviation from correct timing that is considered by microprocessor 46 to be within the specified temporal tolerance for the purpose of illuminating "N in a row" indicator 32. A repetition rate select potentiometer 76 may be set by the user to indicate a desired repetition rate of the reference signal. In the illustrated embodiment, the reference signal may be played back as frequently as several times in one second down to a repetition rate of less than one pulse in 15 seconds Thus, it is seen that the present invention provides a wide range of applications for the purposes of enhancing the time alignment in users. The invention may be utilized for such wide ranging applications as enhancing motor skills in handicapped individuals, improving musical performance capabilities among band members and an educational skill developing game. The invention may further find application in the testing of an individual's reflex coordination in order to, for example, determine the skills that the individual may bring to bear in operating a motor vehicle. Thus, a system could be installed in a driver's licensing office in order to provide a quick and non-intrusive determination of whether the individual's reflexes are sufficient to operate a motor vehicle. Such use may be extended to determining whether an individual is capable of performing his or her occupation in lieu of intrusive drug testing. The invention may additionally find application in the training of animals. For example, the invention may be used in the training of horses, whales, dolphins and other highly intelligent animals.

Changes and modifications to the specifically described embodiments can be carried out without departing from the principles of the invention, which is intended to be limited only by the scope of the appended claims, as interpreted according to the principles of patent law including the doctrine of equivalents.

The embodiments of the invention in which an exclusive property or privilege is claimed are defined as follows:

1. A neuro-motor coordination measuring and enhancing apparatus, comprising:

a user operable trigger device which receives a user manipulation of said trigger device;

an aural output which provides an aural signal to a user; and a control including an aural generator which is responsive to user manipulation of said trigger device for causing said aural output to generate aural signals, said control generating a reference signal having occurrences separated by a predetermined time interval and determining a temporal relationship between user manipulations of said trigger device and occurrences of said reference signal, said control causing said aural output to provide aural signals including said reference signal and a guidance aural signal that is a function of said temporal relationship, wherein said guidance aural signal is provided substantially concurrently with a user manipulation of said trigger device in order to draw the user into time alignment with the occurrences of the reference signal for extended periods thereby improving the user's neurological functionality.

2. The apparatus in claim 1 wherein said aural output includes at least one audio speaker and wherein said aural output combines said reference signal and said guidance aural signal into a combined signal and supplies the combined signal to said at least one audio speaker.

3. The apparatus in claim 2 wherein said guidance aural signal is a tactile signal.

4. The apparatus in claim 1 wherein said trigger device is one of a touch sensor, an impact sensor, a motion sensor, a proximity sensor, a pressure sensor and a microphone.

5. The apparatus in claim 4 wherein said trigger device is configured to be mounted to a hand of a user.

6. The apparatus in claim 4 wherein said trigger device is configured to be mounted to a foot of a user.

7. The apparatus in claim 1 wherein said control is a programmable microprocessor.

8. The apparatus in claim 1 wherein said guidance aural signal varies in proportion to said temporal relationship.

9. The apparatus in claim 8 wherein said guidance aural signal varies in one of pitch, tonality and amplitude in proportion to said temporal relationship.

10. The apparatus of claim 1 wherein said reference signal is an audio tone and wherein said audio tone varies from said guidance aural signal in proportion to said temporal relationship.

11. The apparatus of claim 10 wherein said guidance aural signal varies from said audio tone as a function of the temporal relationship between said response and the predetermined time interval since the last occurrence of said reference signal.

12. A method of measuring and enhancing the neuro-motor coordination of a user, said method including the steps of:

presenting to the user repetitive occurrences of a non-visual reference signal, said occurrences separated by a predetermined time interval;

receiving from the user with a trigger device a conscious physical response to the user's prediction of the lapse of said predetermined time interval since the last occurrence of said reference signal;

determining the temporal relationship between the conscious physical response of the user and the predetermined time interval since the last occurrence of the reference signal; and generating a non-visual guidance signal that is a function of said temporal relationship and presenting said guidance signal to the user substantially concurrently with the user's response in order to draw the user into time alignment with the occurrence of the reference signal and to induce repetitive physical interactivity with the reference signal to thereby enhance the neuro-motor coordination of the user.

13. The method of claim 12 wherein said reference signal and said guidance signal are aural.

14. The method of claim 12 further including the step of providing a reward signal to the user when said temporal relationship is within a particular range.

15. The method of claim 14 further including the step of varying said particular range.

16. The method of claim 12 wherein said non-visual guidance signal varies in proportion to said temporal relationship.

17. The method in claim 12 wherein said non-visual guidance signal is an aural signal that varies in one of pitch, tonality and amplitude in proportion to said temporal relationship.

18. The method in claim 17 wherein said periodic reference signal is an audio tone and wherein said audio tone varies from said aural signal in proportion to said temporal relationship.

19. The method in claim 18 wherein said aural signal varies from said audio tone as a function of the temporal relationship between said response and the predetermined time interval since the last occurrence of said periodic reference signal.

20. The method in claim 12 wherein said non-visual guidance signal is a tactile signal.

* * * * *